(12) United States Patent
Gilman (10) Patent No.: US 8,841,429 B2
(45) Date of Patent: Sep. 23, 2014

(54) NUCLEIC ACID LIGANDS AGAINST INFECTIOUS PRIONS

(75) Inventor: Vladimir Leo Gilman, Westford, MA (US)

(73) Assignee: Vivonics, Inc., Waltham, MA (US)

( * ) Notice: Subject to any disclaimer, the term of this patent is extended or adjusted under 35 U.S.C. 154(b) by 690 days.

(21) Appl. No.: 12/611,473

(22) Filed: Nov. 3, 2009

(65) Prior Publication Data

US 2011/0104668 A1 May 5, 2011

(51) Int. Cl.
*C07H 21/04* (2006.01)
*C07H 21/02* (2006.01)
*C07K 14/47* (2006.01)
*C12N 15/115* (2010.01)
*C12Q 1/68* (2006.01)
*A61K 38/00* (2006.01)

(52) U.S. Cl.
CPC .............. *C07K 14/47* (2013.01); *C12N 15/115* (2013.01); *C12Q 1/6816* (2013.01); *C12Q 1/6883* (2013.01); *A61K 38/00* (2013.01); *C12N 2310/16* (2013.01)
USPC ........................................ 536/23.1; 536/24.3

(58) Field of Classification Search
CPC ....... C07K 14/47; C12Q 1/6883; A61K 38/00
See application file for complete search history.

(56) References Cited

U.S. PATENT DOCUMENTS

| | | |
|---|---|---|
| 5,270,163 A | 12/1993 | Gold et al. |
| 5,459,015 A | 10/1995 | Janjic et al. |
| 5,472,841 A | 12/1995 | Jayasena et al. |
| 5,475,096 A | 12/1995 | Gold et al. |
| 5,476,766 A | 12/1995 | Gold et al. |
| 5,496,938 A | 3/1996 | Gold et al. |
| 5,503,978 A | 4/1996 | Schneider et al. |
| 5,527,894 A | 6/1996 | Gold et al. |
| 5,543,293 A | 8/1996 | Gold et al. |
| 5,567,588 A | 10/1996 | Gold et al. |
| 5,580,737 A | 12/1996 | Polisky et al. |
| 5,587,468 A | 12/1996 | Allen et al. |
| 5,595,877 A | 1/1997 | Gold et al. |
| 5,622,828 A | 4/1997 | Parma et al. |
| 5,629,155 A | 5/1997 | Wiegand et al. |
| 5,635,615 A | 6/1997 | Allen et al. |
| 5,637,459 A | 6/1997 | Burke et al. |
| 5,637,461 A | 6/1997 | Gold et al. |
| 5,637,682 A | 6/1997 | Nieuwlandt et al. |
| 5,639,868 A | 6/1997 | Janjic et al. |
| 5,641,629 A | 6/1997 | Pitner et al. |
| 5,648,214 A | 7/1997 | Nieuwlandt et al. |
| 5,650,275 A | 7/1997 | Pitner et al. |
| 5,654,151 A | 8/1997 | Allen et al. |
| 5,660,985 A | 8/1997 | Pieken et al. |
| 5,668,264 A | 9/1997 | Janjic et al. |
| 5,670,637 A | 9/1997 | Gold et al. |
| 5,674,685 A | 10/1997 | Janjic et al. |
| 5,683,867 A | 11/1997 | Biesecker et al. |
| 5,686,592 A | 11/1997 | Wiegand et al. |
| 5,688,935 A | 11/1997 | Stephens et al. |
| 5,693,502 A | 12/1997 | Gold et al. |
| 5,696,249 A | 12/1997 | Gold et al. |
| 5,705,337 A | 1/1998 | Gold et al. |
| 5,707,796 A | 1/1998 | Gold et al. |
| 5,712,375 A | 1/1998 | Jensen et al. |
| 5,723,289 A | 3/1998 | Eaton et al. |
| 5,723,592 A | 3/1998 | Eaton et al. |
| 5,723,594 A | 3/1998 | Janjic et al. |
| 5,726,017 A | 3/1998 | Lochrie et al. |
| 5,731,144 A | 3/1998 | Toothman et al. |
| 5,731,424 A | 3/1998 | Toothman et al. |
| 5,734,034 A | 3/1998 | Jayasena et al. |
| 5,750,342 A | 5/1998 | Stephens et al. |
| 5,756,287 A | 5/1998 | Allen et al. |
| 5,763,173 A | 6/1998 | Gold et al. |
| 5,763,177 A | 6/1998 | Gold et al. |
| 5,763,566 A | 6/1998 | Jensen et al. |
| 5,763,595 A | 6/1998 | Gold et al. |
| 5,766,853 A | 6/1998 | Parma et al. |
| 5,773,598 A | 6/1998 | Burke et al. |
| 5,780,228 A | 7/1998 | Parma et al. |
| 5,786,462 A | 7/1998 | Schneider et al. |
| 5,789,157 A | 8/1998 | Jensen et al. |
| 5,789,160 A | 8/1998 | Eaton et al. |
| 5,789,163 A | 8/1998 | Drolet et al. |
| 5,795,721 A | 8/1998 | Rabin et al. |
| 5,811,533 A | 9/1998 | Gold et al. |
| 5,817,785 A | 10/1998 | Gold et al. |
| 5,837,456 A | 11/1998 | Gold et al. |
| 5,837,834 A | 11/1998 | Pagratis et al. |
| 5,843,653 A | 12/1998 | Gold et al. |
| 5,843,701 A | 12/1998 | Gold et al. |
| 5,846,713 A | 12/1998 | Pagratis et al. |
| 5,849,479 A | 12/1998 | Janjic et al. |
| 5,849,890 A | 12/1998 | Gold et al. |
| 5,853,984 A | 12/1998 | Davis et al. |
| 5,856,099 A | 1/1999 | Miraglia et al. |
| 5,856,455 A | 1/1999 | Cook |
| 5,858,660 A | 1/1999 | Eaton et al. |
| 5,859,221 A | 1/1999 | Cook et al. |

(Continued)

OTHER PUBLICATIONS

Vivekananda (Laboratory Investigation (2006) vol. 86, pp. 610-618).*

*Primary Examiner* — Steven Pohnert
(74) *Attorney, Agent, or Firm* — Brown Rudnick LLP; Thomas C. Meyers (57) ABSTRACT

The invention generally relates to nucleic acid ligands that specifically bind to infectious prions, and methods of diagnosing a transmissible spongiform encephalopathy disease in a subject. In certain embodiments, the invention provides an isolated nucleic acid ligand that binds to an infectious prion. In other embodiments, the invention provides a method for diagnosing a transmissible spongiform encephalopathy disease in a subject including obtaining a tissue or body fluid sample from a subject, contacting the tissue or body fluid with a nucleic acid ligand that binds to an infectious prion, thereby detecting the infectious prion in the sample, and diagnosing the transmissible spongiform encephalopathy disease based on results of the contacting step.

6 Claims, 5 Drawing Sheets

(56) References Cited

U.S. PATENT DOCUMENTS

| | | | |
|---|---|---|---|
| 5,859,228 A | 1/1999 | Janjic et al. |
| 5,861,254 A | 1/1999 | Schneider et al. |
| 5,864,026 A | 1/1999 | Jensen et al. |
| 5,869,641 A | 2/1999 | Jayasena et al. |
| 5,874,218 A | 2/1999 | Drolet et al. |
| 5,874,532 A | 2/1999 | Pieken et al. |
| 5,874,557 A | 2/1999 | Gold et al. |
| 5,914,269 A | 6/1999 | Bennett et al. |
| 5,958,691 A | 9/1999 | Pieken et al. |
| 5,962,219 A | 10/1999 | Gold et al. |
| 5,965,722 A | 10/1999 | Ecker et al. |
| 5,972,599 A | 10/1999 | Tasset et al. |
| 5,985,662 A | 11/1999 | Anderson et al. |
| 5,989,823 A | 11/1999 | Jayasena et al. |
| 5,998,142 A | 12/1999 | Gold et al. |
| 6,001,577 A | 12/1999 | Gold et al. |
| 6,001,966 A | 12/1999 | Pieken et al. |
| 6,001,988 A | 12/1999 | Parma et al. |
| 6,005,087 A | 12/1999 | Cook et al. |
| 6,011,020 A | 1/2000 | Gold et al. |
| 6,013,443 A | 1/2000 | Heilig et al. |
| 6,020,130 A | 2/2000 | Gold et al. |
| 6,028,186 A | 2/2000 | Tasset et al. |
| 6,030,776 A | 2/2000 | Eaton et al. |
| 6,051,698 A | 4/2000 | Janjic et al. |
| 6,077,833 A | 6/2000 | Bennett et al. |
| 6,083,696 A | 7/2000 | Biesecker et al. |
| 6,107,094 A | 8/2000 | Crooke |
| 6,110,900 A | 8/2000 | Gold et al. |
| 6,114,120 A | 9/2000 | Jensen et al. |
| 6,124,449 A | 9/2000 | Gold et al. |
| 6,127,119 A | 10/2000 | Stephens et al. |
| 6,140,490 A | 10/2000 | Biesecker et al. |
| 6,146,829 A | 11/2000 | Cook et al. |
| 6,147,204 A | 11/2000 | Gold et al. |
| 6,168,778 B1 | 1/2001 | Janjic et al. |
| 6,171,795 B1 | 1/2001 | Korman et al. |
| 6,177,555 B1 | 1/2001 | Jayasena et al. |
| 6,177,557 B1 | 1/2001 | Janjic et al. |
| 6,183,967 B1 | 2/2001 | Jayasena et al. |
| 6,184,364 B1 | 2/2001 | Pieken et al. |
| 6,187,585 B1 | 2/2001 | Bennett et al. |
| 6,194,550 B1 | 2/2001 | Gold et al. |
| 6,207,816 B1 | 3/2001 | Gold et al. |
| 6,229,002 B1 | 5/2001 | Janjic et al. |
| 6,232,071 B1 | 5/2001 | Hicke et al. |
| 6,242,246 B1 | 6/2001 | Gold et al. |
| 6,261,774 B1 | 7/2001 | Pagratis et al. |
| 6,261,783 B1 | 7/2001 | Jayasena et al. |
| 6,271,029 B1 | 8/2001 | Bennett et al. |
| 6,277,603 B1 | 8/2001 | Cook |
| 6,280,932 B1 | 8/2001 | Parma et al. |
| 6,280,943 B1 | 8/2001 | Drolet et al. |
| 6,287,860 B1 | 9/2001 | Monia et al. |
| 6,291,184 B1 | 9/2001 | Gold et al. |
| 6,300,074 B1 | 10/2001 | Gold et al. |
| 6,300,132 B1 | 10/2001 | Monia et al. |
| 6,316,259 B1 | 11/2001 | Monia et al. |
| 6,326,199 B1 | 12/2001 | Cook et al. |
| 6,326,358 B1 | 12/2001 | Manoharan |
| 6,329,145 B1 | 12/2001 | Janjic et al. |
| 6,329,146 B1 | 12/2001 | Crooke et al. |
| 6,331,394 B1 | 12/2001 | Ruckman et al. |
| 6,331,398 B1 | 12/2001 | Gold et al. |
| 6,344,318 B1 | 2/2002 | Gold et al. |
| 6,344,321 B1 | 2/2002 | Rabin et al. |
| 6,346,611 B1 | 2/2002 | Pagratis et al. |
| 6,359,124 B1 | 3/2002 | Ecker et al. |
| 6,376,190 B1 | 4/2002 | Gold et al. |
| 6,376,474 B1 | 4/2002 | Heilig et al. |
| 6,380,368 B1 | 4/2002 | Froehler et al. |
| 6,387,620 B1 | 5/2002 | Smith et al. |
| 6,387,635 B1 | 5/2002 | Drolet et al. |
| 6,395,888 B1 | 5/2002 | Biesecker et al. |
| 6,410,702 B1 | 6/2002 | Swaminathan et al. |
| 6,426,335 B1 | 7/2002 | Janjic et al. |
| 6,428,956 B1 | 8/2002 | Crooke et al. |
| 6,458,539 B1 | 10/2002 | Gold et al. |
| 6,458,543 B1 | 10/2002 | Gold et al. |
| 6,465,188 B1 | 10/2002 | Gold et al. |
| 6,465,189 B2 | 10/2002 | Biesecker et al. |
| 6,482,594 B1 | 11/2002 | Gold et al. |
| 6,503,715 B1 | 1/2003 | Gold et al. |
| 6,506,887 B1 | 1/2003 | Smith et al. |
| 6,531,286 B2 | 3/2003 | Jayasena et al. |
| 6,531,584 B1 | 3/2003 | Cook et al. |
| 6,544,776 B1 | 4/2003 | Gold et al. |
| 6,544,959 B1 | 4/2003 | Parma et al. |
| 6,566,343 B2 | 5/2003 | Biesecker et al. |
| 6,569,620 B1 | 5/2003 | Gold et al. |
| 6,569,630 B1 * | 5/2003 | Vivekananda et al. ............ 435/6 |
| 6,582,918 B2 | 6/2003 | Janjic et al. |
| 6,596,491 B2 | 7/2003 | Hicke et al. |
| 6,613,526 B2 | 9/2003 | Heilig et al. |
| 6,656,690 B2 | 12/2003 | Crooke et al. |
| 6,670,132 B2 | 12/2003 | Janjic et al. |
| 6,673,553 B2 | 1/2004 | Drolet et al. |
| 6,682,886 B1 | 1/2004 | Gold |
| 6,683,166 B2 | 1/2004 | Swaminathan et al. |
| 6,696,252 B2 | 2/2004 | Gold et al. |
| 6,706,482 B2 | 3/2004 | Smith et al. |
| 6,713,616 B2 | 3/2004 | Pagratis et al. |
| 6,716,580 B2 | 4/2004 | Gold et al. |
| 6,716,583 B2 | 4/2004 | Gold et al. |
| 6,730,482 B2 | 5/2004 | Gold et al. |
| 6,737,236 B1 | 5/2004 | Pieken et al. |
| 6,747,014 B2 | 6/2004 | Teng et al. |
| 6,759,392 B1 | 7/2004 | Janjic et al. |
| 6,762,290 B1 | 7/2004 | Janjic et al. |
| 6,822,089 B1 | 11/2004 | Sanghvi et al. |
| 6,841,539 B1 | 1/2005 | Mehta et al. |
| 6,855,496 B2 | 2/2005 | Pagratis et al. |
| 6,933,116 B2 | 8/2005 | Gold et al. |
| 6,962,783 B2 | 11/2005 | Froehler et al. |
| 6,962,784 B2 | 11/2005 | Janjic et al. |
| 6,969,763 B1 | 11/2005 | Ecker et al. |
| 7,005,260 B1 | 2/2006 | Hicke et al. |
| 7,015,315 B1 | 3/2006 | Cook et al. |
| 7,056,896 B2 | 6/2006 | Manoharan |
| 7,057,027 B2 | 6/2006 | Froehler et al. |
| 7,087,735 B2 | 8/2006 | Gold |
| 7,094,535 B2 | 8/2006 | Ruckman et al. |
| 7,125,660 B2 | 10/2006 | Stanton et al. |
| 7,153,948 B2 | 12/2006 | Gold et al. |
| 7,176,295 B2 | 2/2007 | Biesecker et al. |
| 7,196,069 B2 | 3/2007 | Janjic et al. |
| 7,232,807 B2 * | 6/2007 | Grossman et al. ............ 514/44 R |
| 7,258,980 B2 | 8/2007 | Janjic et al. |
| 6,875,593 B2 | 4/2008 | Froehler et al. |
| 7,368,236 B2 | 5/2008 | Gold et al. |
| 7,399,752 B2 | 7/2008 | Parma et al. |
| 7,432,249 B2 | 10/2008 | Crooke |
| 7,432,250 B2 | 10/2008 | Crooke |
| 7,538,211 B2 | 5/2009 | Benedict et al. |
| 7,566,701 B2 | 7/2009 | Diener et al. |
| 7,579,450 B2 | 8/2009 | Burmeister et al. |
| 7,579,456 B2 | 8/2009 | Benedict et al. |
| 7,589,073 B2 | 9/2009 | Diener et al. |
| 7,629,151 B2 | 12/2009 | Gold et al. |
| 7,629,321 B2 | 12/2009 | Crooke |
| 7,695,902 B2 | 4/2010 | Crooke |
| 7,709,192 B2 | 5/2010 | Gold et al. |
| 2001/0055773 A1 | 12/2001 | Jayasena et al. |
| 2002/0038000 A1 | 3/2002 | Gold et al. |
| 2002/0055113 A1 | 5/2002 | Drolet et al. |
| 2002/0064780 A1 | 5/2002 | Gold et al. |
| 2002/0077306 A1 | 6/2002 | Dinkelborg et al. |
| 2002/0102572 A1 | 8/2002 | Crooke et al. |
| 2002/0102599 A1 | 8/2002 | Smith et al. |
| 2002/0106652 A1 | 8/2002 | Gold et al. |
| 2002/0137087 A1 | 9/2002 | Drolet et al. |
| 2002/0150536 A1 | 10/2002 | Ruckman et al. |
| 2002/0172962 A1 | 11/2002 | Gold et al. |
| 2002/0197617 A1 | 12/2002 | Janjic et al. |

(56) References Cited

U.S. PATENT DOCUMENTS

| | | |
|---|---|---|
| 2003/0003461 A1 | 1/2003 | Pagratis et al. |
| 2003/0027781 A1 | 2/2003 | Heilig et al. |
| 2003/0032785 A1 | 2/2003 | Gold et al. |
| 2003/0036642 A1 | 2/2003 | Janjic et al. |
| 2003/0044818 A1 | 3/2003 | Gold et al. |
| 2003/0049644 A1 | 3/2003 | Rabin et al. |
| 2003/0054360 A1 | 3/2003 | Gold et al. |
| 2003/0059769 A1 | 3/2003 | Parma et al. |
| 2003/0064943 A1 | 4/2003 | Pagratis et al. |
| 2003/0077646 A1 | 4/2003 | Biesecker et al. |
| 2003/0078221 A1 | 4/2003 | Biesecker et al. |
| 2003/0087301 A1 | 5/2003 | Smith et al. |
| 2003/0104377 A1 | 6/2003 | Hicke et al. |
| 2003/0114404 A1 | 6/2003 | Janjic et al. |
| 2003/0125263 A1 | 7/2003 | Gold et al. |
| 2003/0157487 A1 | 8/2003 | Gold et al. |
| 2003/0162216 A1 | 8/2003 | Gold et al. |
| 2003/0176680 A1 | 9/2003 | Gold et al. |
| 2003/0180744 A1 | 9/2003 | Gold et al. |
| 2003/0186231 A1 | 10/2003 | Gold et al. |
| 2003/0191084 A1 | 10/2003 | Biesecker et al. |
| 2003/0198989 A1 | 10/2003 | Gold et al. |
| 2003/0219803 A1 | 11/2003 | Jayasena et al. |
| 2004/0043923 A1 | 3/2004 | Parma et al. |
| 2004/0053271 A1 | 3/2004 | Drolet et al. |
| 2004/0058884 A1 | 3/2004 | Hicke et al. |
| 2004/0091931 A1 | 5/2004 | Gold |
| 2004/0101854 A1 | 5/2004 | Bennett et al. |
| 2004/0106129 A1 | 6/2004 | Crook et al. |
| 2004/0106145 A1 | 6/2004 | Gold et al. |
| 2004/0132067 A1 | 7/2004 | Gold et al. |
| 2004/0162259 A1 | 8/2004 | Wedel et al. |
| 2004/0192632 A1 | 9/2004 | Janjic et al. |
| 2004/0220395 A1 | 11/2004 | Froehler et al. |
| 2004/0224915 A1 | 11/2004 | Janjic et al. |
| 2004/0229831 A1 | 11/2004 | Teng et al. |
| 2004/0241731 A1 | 12/2004 | Gold et al. |
| 2004/0258656 A1 | 12/2004 | Pagratis et al. |
| 2005/0042273 A1 | 2/2005 | Janjic et al. |
| 2005/0043265 A1 | 2/2005 | Janjic et al. |
| 2005/0048521 A1 | 3/2005 | Janjic et al. |
| 2005/0112585 A1 | 5/2005 | Zichi et al. |
| 2005/0136474 A1 | 6/2005 | Pagratis et al. |
| 2005/0164974 A1 | 7/2005 | Gold et al. |
| 2005/0208528 A1 | 9/2005 | Krotz et al. |
| 2006/0057573 A1 | 3/2006 | Gold et al. |
| 2006/0079477 A1 | 4/2006 | Biesecker et al. |
| 2006/0084797 A1 | 4/2006 | Pagratis et al. |
| 2006/0088877 A1 | 4/2006 | Gold et al. |
| 2006/0105378 A1 | 5/2006 | Hicke et al. |
| 2006/0147987 A1 | 7/2006 | Gold |
| 2006/0148748 A1 | 7/2006 | Rabin et al. |
| 2006/0229273 A1 | 10/2006 | Gold et al. |
| 2007/0010473 A1 | 1/2007 | Ruckman et al. |
| 2007/0134715 A1 | 6/2007 | Biesecker et al. |
| 2007/0166740 A1 | 7/2007 | Heil et al. |
| 2007/0166741 A1 | 7/2007 | Heil et al. |
| 2007/0166742 A1 | 7/2007 | Gold et al. |
| 2007/0249551 A1 | 10/2007 | Teng et al. |
| 2008/0160535 A1 | 7/2008 | Gold et al. |
| 2008/0207883 A1 | 8/2008 | Janjic et al. |
| 2009/0004667 A1 | 1/2009 | Zichi et al. |
| 2009/0042206 A1 | 2/2009 | Schneider et al. |
| 2009/0075922 A1 | 3/2009 | Rabin et al. |
| 2009/0098549 A1 | 4/2009 | Schneider et al. |
| 2009/0118481 A1 | 5/2009 | Parma et al. |
| 2009/0136953 A1 | 5/2009 | Gold et al. |
| 2009/0149643 A1 | 6/2009 | Diener et al. |
| 2009/0203766 A1 | 8/2009 | Gilbert et al. |
| 2009/0326045 A1 | 12/2009 | Mehta et al. |
| 2010/0029922 A1 | 2/2010 | Janjic et al. |
| 2010/0041866 A1 | 2/2010 | Hatala et al. |
| 2010/0055695 A1 | 3/2010 | Zichi et al. |
| 2010/0070191 A1 | 3/2010 | Gold et al. |
| 2010/0086948 A1 | 4/2010 | Gold et al. |

* cited by examiner

| | Well | Well Identifier | Peak ID | Melt Temp |
|---|---|---|---|---|
| —— | A01 | oligo 1 HOH | A1.1 | 78.0 |
| | | | A1.2 | 65.5 |
| ------ | A02 | oligo 1 0 (NBH) | No Peak | |
| — — — | A03 | oligo 1 $10^{-6}$ | A3.1 | 73.5 |
| — — | A04 | oligo 1 $10^{-5}$ | A4.1 | 74.0 |
| —··— | A05 | oligo 1 $10^{-4}$ | A5.1 | 74.0 |
| ········ | A06 | oligo 1 $10^{-3}$ | A6.1 | 73.0 |
| —···— | A07 | aptamers only | No Peak | |
| ····· | B01 | oligo 2 HOH | B1.1 | 77.0 |
| | | | B1.2 | 64.5 |
| ········ | B02 | oligo 2 0 (NBH) | No Peak | |
| — — — | B03 | oligo 2 $10^{-6}$ | B3.1 | 78.0 |
| · — · | B04 | oligo 2 $10^{-5}$ | B4.1 | 78.5 |

NUCLEIC ACID LIGANDS AGAINST INFECTIOUS PRIONS

FIELD OF THE INVENTION

The invention generally relates to nucleic acid ligands that specifically bind to infectious prions, and methods of diagnosing a transmissible spongiform encephalopathy disease in a subject.

BACKGROUND

Native or cellular prion protein, $PrP^C$, is widely distributed throughout mammals and has a particularly well-conserved amino acid sequence and protein structure. Infectious prions, $PrP^{Sc}$, are composed of a modified form of the normal cellular prion protein. It is thought that a post-translational conformational change is involved in the conversion of non-infectious $PrP^C$ to infectious $PrP^{Sc}$ during which α-helices are transformed into β-sheets. $PrP^C$ contains three α-helices and has little β-sheet structure, while $PrP^{Sc}$ is abundant in β-sheet. Infectious prions are resistant to proteases, the enzymes in the body that can normally break down proteins.

The conversion of $PrP^C$ to $PrP^{Sc}$ leads to development of transmissible spongiform encephalopathies (TSEs) during which $PrP^{Sc}$ accumulates in the central nervous system and is accompanied by neuropathologic changes and neurological dysfunction. Infectious prions cause neurodegenerative disease by aggregating extracellularly within the central nervous system to form plaques known as amyloid that disrupt the normal tissue structure. This disruption is characterized by holes in the tissue with resultant spongy architecture due to vacuole formation in neurons. Other histological changes include astrogliosis and absence of an inflammatory reaction. While the incubation period for prion diseases is generally quite long, once symptoms appear the disease progresses rapidly, leading to brain damage and death. Neurodegenerative symptoms can include convulsions, dementia, ataxia (balance and coordination dysfunction), and behavioral or personality changes.

Specific examples of TSEs include scrapie, which affects sheep and goats; bovine spongiform encephalopathy (BSE); transmissible mink encephalopathy, feline spongiform encephalopathy and chronic wasting disease (CWD). In humans, TSE diseases may present themselves as kuru, Creutzfeldt-Jakob disease (CJD), Gerstmann-Straussler-Scheinker Syndrome (GSS), fatal insomnia, and variant Creutzfeldt-Jakob disease (vCJD).

No therapeutic agent exists to impede infectious prion propagation, and thus human TSE diseases are 100% fatal. A characteristic of all TSEs is the lack of a measurable host immune response to the agent. Consequently, no antibodies specific for TSEs have been identified. Moreover, the lack of a known nucleic acid sequence precludes the use of polymerase chain reaction based diagnostic methods. Thus, no conventional serologic test may be used to identify infected animals.

Methodologies that can readily separate or that can distinguish between two or more different conformational forms of a protein, e.g., $PrP^C$ and $PrP^{Sc}$, are needed to understand the process of conversion and to find structures that will specifically interact with the disease associated form. There also remains a need to identify high affinity binding materials that are specific for the conformationally altered protein and especially forms associated with disease.

SUMMARY

The invention generally relates to nucleic acid ligands that specifically bind to infectious prions. A nucleic acid ligand (aptamer) is a nucleic acid macromolecule (e.g., DNA or RNA) that binds tightly to a specific molecular target. Like all nucleic acids, a particular nucleic acid ligand may be described by a linear sequence of nucleotides (A, U, T, C and G), typically 15-40 nucleotides long. Binding of a nucleic acid ligand to a target molecule is not determined by nucleic acid base pairing. See, for example, Jayasena, Clin. Chem. 45(9):1628-1650, 1999 and Baldrich et al., Anal. Chem. 2004; 76(23):7053-7063. In solution, the chain of nucleotides forms intramolecular interactions that fold the molecule into a complex three-dimensional shape. The shape of the nucleic acid ligand allows it to bind tightly against the surface of its target molecule. In addition to exhibiting remarkable specificity, nucleic acid ligands generally bind their targets with very high affinity, e.g., the majority of anti-protein nucleic acid ligands have equilibrium dissociation constants in the femtoomolar to low nanomolar range.

The nucleic acid ligands of the invention can distinguish between non-infection prions and infectious prions in a sample from patients afflicted with human TSEs and animals afflicted with scrapie, BSE and CWD. Thus, nucleic acid ligands of the invention are useful for detecting, binding to, isolating, removing, eliminating, extracting and separating an infectious prion protein in or from a sample, such as a biological fluid or an environmental sample.

An aspect of the invention provides isolated nucleic acid ligands that bind to an infectious prion. The nucleic acid ligands may be single stranded or double stranded. The nucleic acid ligands may be DNA or RNA. In certain embodiments, the nucleic acid ligands include a nucleotide sequence selected from the group consisting of SEQ ID NO: 1 and SEQ ID NO: 2. In other embodiments, the nucleic acid ligands include an RNA sequence transcribed from a nucleotide sequence selected from the group consisting of SEQ ID NO: 1 and SEQ ID NO: 2. The nucleic acid ligands may further include a detectable label, such as a fluorescent label.

Another aspect of the invention provides a method for diagnosing a transmissible spongiform encephalopathy disease (TSE) in a subject including providing a tissue or body fluid sample from a subject, contacting the tissue or body fluid with a nucleic acid ligand that binds to an infectious prion, thereby detecting the infectious prion in the sample, and diagnosing the transmissible spongiform encephalopathy disease based on results of the contacting step. The subject may be a mammal such as a human.

TSEs that afflict humans include Creutzfeldt-Jakob Disease (CJD); Variant Creutzfeldt-Jakob Disease (vCJD); Gerstmann-Straussler-Scheinker Syndrome; Fatal Familial Insomnia; and Kuru. TSEs that afflict other mammals, such as deer, pigs, cows, sheep, or goats, include Bovine Spongiform Encephalopathy (BSE); Chronic Wasting Disease (CWD); Scrapie; Transmissible mink encephalopathy; Feline spongiform encephalopathy; and Ungulate spongiform encephalopathy.

Another aspect of the invention provides isolated nucleotide sequences including SEQ ID NO: 1 or SEQ ID NO: 2, or nucleotide sequences substantially identical thereto. The nucleotide sequences of the invention may further include a detectable label, such as a fluorescent label. The isolated nucleotide sequences may bind to an infectious prion.

Certain embodiments provide a polypeptide encoded by a nucleotide sequence including SEQ ID NO: 1, SEQ ID NO: 2, or nucleotide sequences substantially identical thereto. The invention also provides a vector include a nucleotide sequence having SEQ ID NO: 1, SEQ ID NO: 2, or nucleotide sequences substantially identical thereto, operably linked to an expression control element. The invention also provides isolated host cells transformed with a vector including a nucleotide sequence having SEQ ID NO: 1, SEQ ID NO: 2, or nucleotide sequences substantially identical thereto. Certain embodiments provide an isolated nucleotide sequence that hybridizes to a nucleotide sequence having SEQ ID NO: 1, SEQ ID NO: 2, or nucleotide sequences substantially identical thereto under high stringency conditions. Other embodiments provide an isolated nucleotide sequence that is complementary to a nucleotide sequence having SEQ ID NO: 1, SEQ ID NO: 2, or nucleotide sequences substantially identical thereto.

BRIEF DESCRIPTION OF THE DRAWINGS

FIG. 1 panels A and B are photographs of a gel containing isolated nucleic acid ligands bound to infectious prions. Panel A shows a DNA titration gel showing band density as function of DNA oligomer concentration. Panel B shows a gel obtained by sequential application and electrophoresis of protein and DNA randomer solutions. The area of $PrP^{Sc}$ protein stained with EB due to presence of DNA is circled.

FIG. 6 shows confirmation of specific PCR product after amplification of the nucleic acid ligands. Panel A is a graph showing a melt curve analysis. Panel B shows an agarose gel electrophoresis.

DETAILED DESCRIPTION

The invention generally relates to nucleic acid ligands that specifically bind to infectious prions. This invention includes nucleic acid sequences that are substantially homologous to and that have substantially the same ability to bind infectious prions as the specific nucleic acid ligands shown in Examples below. Substantially homologous refers to a degree of primary sequence homology in excess of about 70%, most preferably in excess of about 80%. Substantially the same ability to bind an infectious prion refers to affinity within about two orders of magnitude of the affinity of the ligands described herein. It is well within the skill of those of ordinary skill in the art to determine whether a given sequence is substantially homologous to those specifically described herein, and has substantially the same ability to bind an infectious prion.

The nucleic acid ligands may be single stranded or double stranded. The nucleic acid ligands may be DNA or RNA. In certain embodiments, the nucleic acid ligands include a nucleotide sequence consisting of SEQ ID NO: 1 or SEQ ID NO: 2. In other embodiments, the nucleic acid ligands include an RNA sequence transcribed from a nucleotide sequence consisting of SEQ ID NO: 1 or SEQ ID NO: 2.

Nucleic acid ligands of the invention were identified by methods described in co-pending and co-owned U.S. patent application Ser. No. 12/611,436, filed Nov. 3, 2009, and entitled "Methods for identifying nucleic acid ligands", the contents of which are incorporated by reference herein in its entirety. Briefly, a candidate mixture of nucleic acids is contacted to an infectious prion. After a sufficient incubation time, a single step selective separation protocol (e.g., gel electrophoresis or HPLC gradient elution) is employed to eliminate undesirable competition for the infectious prion among nucleic acids that bind the infectious prion with greatest affinity, nucleic acids that bind the infectious prion with a lesser affinity, and nucleic acids that do not bind the infectious prion.

The selective separation protocols generate conditions in which the nucleic acids that bind the infectious prion with a lesser affinity and nucleic acids that do not bind the infectious prion cannot form complexes with the infectious prion or can only form complexes with the infectious prion for a short period of time. In contrast, the conditions of the separation protocols allow nucleic acids that bind the infectious prion with greatest affinity to form complexes with the infectious prion and/or bind the infectious prion for the greatest period of time, thereby separating in a single step the nucleic acids with the greatest affinity for the infectious prion, i.e., the nucleic acid ligands of the invention, from the remainder of the nucleic acids of the candidate mixture.

An exemplary separation protocol includes loading the infectious prion into a gradient gel, applying an electric current to cause the infectious prion to migrate to a position in the gel, in which the infectious prion remains immobilized at that position in the gel, loading the aptamer candidate mixture into the gel, and applying an electric current to cause the candidate mixture to migrate through the gel, in which the nucleic acids with the greatest affinity for the target molecule (i.e., nucleic acid ligands of the invention) bind to the infectious prion immobilized in the gel, and the nucleic acids with lesser affinity for the infectious prion and nucleic acids with no affinity for the infectious prion migrate to an end of the gel. The gel segment containing nucleic acid ligand/infectious prion complex is then cut from the gel, and the nucleic acid ligands are then dissociated from the infectious prion using a chaotropic agent.

Another exemplary separation protocol includes incubating the candidate mixture of nucleic acids with a plurality of infectious prions to form nucleic acid/infectious prion complexes, in which the infectious prions are bound to beads, and eluting the nucleic acids from the complexes that have been loaded onto an HPLC column by applying an HPLC gradient profile, in which nucleic acids with the greatest affinity for the infectious prion (i.e., nucleic acid ligands of the invention) elute at an end portion of the gradient profile and the nucleic acids with a lesser affinity for the infectious prion and nucleic acids with no affinity for the infectious prion elute prior to the end portion of the gradient profile. Many different HPLC gradient elution profiles are known in the art. An exemplary HPLC gradient elution profile may include a linear increasing concentration of the infectious prion, in which an end portion of the gradient profile may include a linear increasing concentration of the infectious prion and a chaotropic agent (e.g., urea, guanidinium chloride, $SCN^-$, or LiBr).

After separation, the nucleic acid ligands of the invention may be sequenced. Sequencing may be by any method known in the art. See for example Sanger et al. (Proc Natl Acad Sci USA, 74(12): 5463 67, 1977), Maxam et al. (Proc. Natl. Acad. Sci., 74: 560-564, 1977), and Drmanac, et al. (Nature Biotech., 16:54-58, 1998), which references describe exemplary conventional ensemble sequencing techniques. Also see Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., (PNAS (USA), 100: 3960-3964, 2003), which references describe exemplary single molecule sequencing by synthesis techniques. The contents of each of the references is incorporated by reference herein in its entirety.

The nucleic acid ligands may further include a detectable label, such as radioactive labels, chemoluminescent labels, luminescent labels, phosphorescent labels, fluorescence polarization labels, and charge labels.

In certain embodiments, the detectable label is a fluorescent label. Suitable fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl] naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescently labeled nucleotides may be obtained commercially (e.g., from NEN DuPont, Amersham, and BDL). Alternatively, fluorescently labeled nucleotides may also be produced by various techniques, such as those described in Kambara et al. (Bio/Technol., 6:816-21, 1988); Smith et al. (Nucl. Acid Res., 13:2399-2412, 1985); and Smith et al. (Nature, 321: 674-679, 1986). The fluorescent dye may be linked to the deoxyribose by a linker arm that is easily cleaved by chemical or enzymatic means. There are numerous linkers and methods for attaching labels to nucleotides, as shown in Oligonucleotides and Analogues: A Practical Approach (IRL Press, Oxford, 1991); Zuckerman et al. (Polynucleotides Res., 15: 5305-5321, 1987); Sharma et al. (Polynucleotides Res., 19:3019, 1991); Giusti et al. (PCR Methods and Applications, 2:223-227, 1993); Fung et al. (U.S. Pat. No. 4,757,141); Stabinsky (U.S. Pat. No. 4,739, 044); Agrawal et al. (Tetrahedron Letters, 31:1543-1546, 1990); Sproat et al. (Polynucleotides Res., 15:4837, 1987); and Nelson et al. (Polynucleotides Res., 17:7187-7194, 1989). Extensive guidance exists in the literature for derivatizing fluorophore and quencher molecules for covalent attachment via common reactive groups that may be added to a nucleotide. Many linking moieties and methods for attaching fluorophore moieties to nucleotides also exist, as described in Oligonucleotides and Analogues, supra; Guisti et al., supra; Agrawal et al, supra; and Sproat et al., supra.

Certain chemical modifications of the nucleic acid ligands of the invention may be made to increase the in vivo stability of the nucleic acid ligand or to enhance or to mediate the delivery of the nucleic acid ligand. See, e.g., Pieken et al. (U.S. Pat. No. 5,660,985), the contents of which are incorporated by reference herein in their entirety. Modifications of the nucleic acid ligands contemplated in this invention include, but are not limited to, those that provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to 2-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping. In certain embodiments of the instant invention, the nucleic acid ligands are RNA molecules that are 2'-fluoro (2'-F) modified on the sugar moiety of pyrimidine residues.

Nucleic acid ligands of the invention can further include a nucleotide analog. Exemplary nucleotide analogs include xanthine or hypoxanthine, 5-bromouracil, 2-aminopurine, deoxyinosine, or methylated cytosine, such as 5-methylcytosine, N4-methoxydeoxycytosine, and the like. Also included are bases of polynucleotide mimetics, such as methylated nucleic acids, e.g., 2'-O-methRNA, peptide nucleic acids, locked nucleic acids, modified peptide nucleic acids, and any other structural moiety that acts substantially like a nucleotide or base, for example, by exhibiting base-complementarity with one or more bases that occur in DNA or RNA.

The nucleic acid ligands of the invention are capable of distinguishing between different conformational forms of $PrP^C$ and $PrP^{Sc}$, and thus provide high affinity binding materials that are specific for the conformationally altered protein and especially forms associated with disease. Accordingly, another aspect of the invention provides methods for diagnosing any disease in a subject associated with an infectious prion. In certain embodiments, the invention provides a method for diagnosing a transmissible spongiform encephalopathy disease (TSE) in a subject. The subject may be a mammal such as a human. TSEs that afflict humans include Creutzfeldt-Jakob Disease (CJD); Variant Creutzfeldt-Jakob Disease (vCJD); Gerstmann-Straussler-Scheinker Syndrome; Fatal Familial Insomnia; and Kuru. TSEs that afflict other mammals, such as deer, pigs, cows, sheep, or goats, include Bovine Spongiform Encephalopathy (BSE); Chronic Wasting Disease (CWD); Scrapie; Transmissible mink encephalopathy; Feline spongiform encephalopathy; and Ungulate spongiform encephalopathy.

Methods of the invention include providing a tissue or body fluid sample from a subject. A sample may originate from a mammal, e.g. a human, and includes tissue or body fluid. The sample may also originate from other mammals, such as deer, pigs, cows, sheep, or goats. A tissue is a mass of connected cells and/or extracellular matrix material, e.g. skin tissue, nasal passage tissue, CNS tissue, neural tissue, eye tissue, liver tissue, kidney tissue, placental tissue, mammary gland tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to urine, sputum, stool, mucous, saliva, blood, plasma, serum, serum derivatives, bile, phlegm, sweat, amniotic fluid, mammary fluid, and cerebrospinal fluid (CSF), such as lumbar or ventricular CSF. A sample may also be a fine needle aspirate or biopsied tissue. A sample also may be media containing cells or biological material.

Methods of the invention further include contacting the tissue or body fluid with a nucleic acid ligand that binds to an infectious prion, thereby detecting the infectious prion in the sample. Nucleic acid ligand-based assays are very similar to antibody-based assays but use a nucleic acid ligand instead of an antibody. Similar to an antibody, a nucleic acid ligand has a molecular activity such as having an enzymatic activity or binding to a target molecule at a specific region (i.e., similar to an epitope for an antibody). Thus, any suitable antibody-based technique may be adapted for use with the present methods. Exemplary antibody-based assays that can be adapted for use with nucleic acid ligands include Western blot analysis, radioimmunoassay (RIA), immunofluorescent assay, chemiluminescent assay, or enzyme-linked immunosorbent assay (ELISA). Protocols of these assays are described in Stenman et al. (U.S. Pat. No. 5,976,809), Tamarkin et al. (U.S. Pat. No. 5,965,379), Chen (U.S. Pat. No. 5,571,680), Griffin et al. (U.S. Pat. No. 5,279,956), and Price et al. (U.S. Pat. No. 6,579,684), the contents of each of which are incorporated by reference herein in its entirety. Adaptation of these antibody-based assays for use with nucleic acid ligands is well within the knowledge of one of skill in the art.

An exemplary antibody-based assay that has been adapted for use with a nucleic acid ligand is an ALISA (Aptamer-Linked Immobilized Sorbent Assay) procedure, described in Vivekananda et al. (Lab Invest. 86(6):610-618, 2006), the contents of which are incorporated by reference herein in its entirety. Based on results of the assay, the transmissible spongiform encephalopathy disease is diagnosed.

Another aspect of the invention provides isolated nucleotide sequences including SEQ ID NO: 1 or SEQ ID NO: 2, or nucleotide sequences substantially identical thereto. Examples below describe isolation and purification of the nucleotide sequences of the invention. A nucleic acid or fragment thereof has substantial identity with another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Identity refers to degree of sequence relatedness between two polynucleotide sequences as determined by the identity of the match between two strings of such sequences, such as the full and complete sequence. Identity can be readily calculated. While there exist a number of methods to measure identity between two polynucleotide sequences, the term identity is well known to skilled artisans (see e.g., Computational Molecular Biolog, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Methods commonly employed to determine identity between two sequences include, but are not limited to, those shown in Guide to Huge Computers, Martin J. Bishop, ed., Academic Press, San Diego, 1994, and Carillo, H., and Lipman, D., SIAM J Applied Math. 48:1073 (1988). In certain embodiments, methods to determine identity are designed to give the largest match between the two sequences tested. Such methods are codified in computer programs. Exemplary computer program methods to determine identity between two sequences include, but are not limited to, GCG (Genetics Computer Group, Madison Wis.) program package (Devereux, J., et al., Nucleic Acids Research 12:387 (1984)), BLASTP, BLASTN, FASTA (Altschul, S. F. et al. (1990) J. Mol. Biol. 215:403-410; and Altschul, S. F. et al. (1997) Nucl. Acids Res. 25:3389-3402). The well-known Smith Waterman algorithm may also be used to determine identity.

Aspects of the invention also include nucleotide sequences that hybridize to SEQ ID NO: 1 or SEQ ID NO: 2 under high stringency conditions. Nucleic acid hybridization may be affected by such conditions as salt concentration, temperature, or organic solvents, in addition to base composition, length of complementary strands, and number of nucleotide base mismatches between hybridizing nucleic acids, as is readily appreciated by those skilled in the art. Stringency of hybridization reactions is readily determinable by one of ordinary skill in the art, and generally is an empirical calculation dependent upon sequence length, washing temperature, and salt concentration. In general, longer sequences require higher temperatures for proper annealing, while shorter sequences need lower temperatures. Hybridization generally depends on the ability of denatured DNA to reanneal when complementary strands are present in an environment below its melting temperature. The higher the degree of desired homology between the sequence and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995), the contents of which are incorporated by reference herein in their entirety.

Stringent conditions or high stringency conditions typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 .mu.g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

Moderately stringent conditions may be identified as described by Sambrook et al., Molecular Cloning: A Laboratory Manual, New York: Cold Spring Harbor Press, 1989 (the contents of which are incorporated by reference herein in their entirety), and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37° C. to 50° C. The skilled artisan will recognize how to adjust the temperature, ionic strength, etc. as necessary to accommodate factors such as sequence length and the like.

Isolated nucleotide sequences of the invention may be inserted into vectors for expression in an isolated host cell. In accordance with the present invention nucleotide sequences of the invention may be engineered into recombinant DNA molecules to direct expression of a polypeptide encoded by SEQ ID NO: 1 or SEQ ID NO: 2 in appropriate host cells. To express a biologically active polypeptide, a nucleotide sequence encoding the polypeptide, e.g., SEQ ID NO: 1 or SEQ ID NO: 2, or functional equivalent, is inserted into an appropriate expression vector, i.e., a vector that contains the necessary nucleic acid encoding elements that regulate transcription and translation of the inserted coding sequence, operably linked to the nucleotide sequence encoding the polypeptide amino acid sequence.

Methods that are well known to those skilled in the art are used to construct expression vectors containing a sequence encoding the polypeptide of SEQ ID NO: 1 or SEQ ID NO: 2 operably linked to appropriate transcriptional and translational control elements. These methods include in vitro recombinant DNA techniques, synthetic techniques and in vivo recombination or genetic recombination. Such techniques are described in Sambrook et al., Molecular Cloning: A Laboratory Manual, Cold Spring Harbor Press, Plainview, N.Y., 1989.

A variety of commercially available expression vector/host systems are useful to contain and express a polypeptide encoded by SEQ ID NO: 1 or SEQ ID NO: 2. These include but are not limited to microorganisms such as bacteria transformed with recombinant bacteriophage, plasmid or cosmid DNA expression vectors; yeast transformed with yeast expression vectors; insect cell systems contacted with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti, pBR322, or pET25b plasmid); or animal cell systems. See Ausubel et al., Current Protocols in Molecular Biology, John Wiley & Sons, New York, N.Y., 1989.

Virus vectors include, but are not limited to, adenovirus vectors, lentivirus vectors, adeno-associated virus (AAV) vectors, and helper-dependent adenovirus vectors. Adenovirus packaging vectors are commercially available from American Type Tissue Culture Collection (Manassas, Va.). Methods of constructing adenovirus vectors and using adenovirus vectors are shown in Klein et al., Ophthalmology, 114:253-262, 2007 and van Leeuwen et al., Eur. J. Epidemiol., 18:845-854, 2003. Adenovirus vectors have been used in eukaryotic gene expression (Levrero et al., Gene, 101:195-202, 1991) and vaccine development (Graham et al., Methods in Molecular Biology: Gene Transfer and Expression Protocols 7, (Murray, Ed.), Humana Press, Clifton, N.J., 109-128, 1991). Further, recombinant adenovirus vectors are used for gene therapy (Wu et al., U.S. Pat. No. 7,235,391).

Recombinant adenovirus vectors are generated, for example, from homologous recombination between a shuttle vector and a provirus vector (Wu et al., U.S. Pat. No. 7,235,391). The adenovirus vectors herein are replication defective, for example, are conditionally defective, lacking adenovirus E1 region, and a polynucleotide of SEQ ID NO: 1 or SEQ ID NO: 2 is introduced at the position from which the E1-coding sequences have been removed. The polynucleotide sequence alternatively is inserted in the E3 region, or is inserted in an E4 region using a helper cell line.

Helper cell lines may be derived from human cells such as, 293 human embryonic kidney cells, muscle cells, hematopoietic cells or other human embryonic mesenchymal or epithelial cells. Alternatively, the helper cells may be derived from the cells of other mammalian species that are permissive for human adenovirus, e.g., Vero cells or other monkey embryonic mesenchymal or epithelial cells. Generation and propagation of these replication defective adenovirus vectors using a helper cell line is described in Graham et al, J. Gen. Virol., 36:59-72, 1977.

Lentiviral vector packaging vectors are commercially available from Invitrogen Corporation (Carlsbad Calif.). An HIV-based packaging system for the production of lentiviral vectors is prepared using constructs in Naldini et al., Science 272: 263-267, 1996; Zufferey et al., Nature Biotechnol., 15: 871-875, 1997; and Dull et al., J. Virol. 72: 8463-8471, 1998.

A number of vector constructs are available to be packaged using a system, based on third-generation lentiviral SIN vector backbone (Dull et al., J. Virol. 72: 8463-8471, 1998). For example the vector construct pRRLsinCMVGFPpre contains a 5' LTR in which the HIV promoter sequence has been replaced with that of Rous sarcoma virus (RSV), a self-inactivating 3' LTR containing a deletion in the U3 promoter region, the HIV packaging signal, RRE sequences linked to a marker gene cassette consisting of the Aequora jellyfish green fluorescent protein (GFP) driven by the CMV promoter, and the woodchuck hepatitis virus PRE element, which appears to enhance nuclear export. The GFP marker gene allows quantitation of transfection or transduction efficiency by direct observation of UV fluorescence microscopy or flow cytometry (Kafri et al., Nature Genet., 17: 314-317, 1997 and Sakoda et al., J. Mol. Cell. Cardiol., 31: 2037-2047, 1999).

Manipulation of retroviral nucleic acids to construct a retroviral vector containing the SEQ ID NO: 1 or SEQ ID NO: 2 and packaging cells is accomplished using techniques known in the art. See Ausubel, et al., 1992, Volume 1, Section III (units 9.10.1-9.14.3); Sambrook, et al., 1989. Molecular Cloning: A Laboratory Manual. Second Edition. Cold Spring Harbor Laboratory Press, Cold Spring Harbor, N.Y.; Miller, et al., Biotechniques. 7:981-990, 1989; Eglitis, et al., Biotechniques. 6:608-614, 1988; U.S. Pat. Nos. 4,650,764, 4,861, 719, 4,980,289, 5,122,767, and 5,124,263; and PCT patent publications numbers WO 85/05629, WO 89/07150, WO 90/02797, WO 90/02806, WO 90/13641, WO 92/05266, WO 92/07943, WO 92/14829, and WO 93/14188.

A retroviral vector is constructed and packaged into non-infectious transducing viral particles (virions) using an amphotropic packaging system. Examples of such packaging systems are found in, for example, Miller, et al., Mol. Cell Biol. 6:2895-2902, 1986; Markowitz, et al., J. Virol. 62:1120-1124, 1988; Cosset, et al., J. Virol. 64:1070-1078, 1990; U.S. Pat. Nos. 4,650,764, 4,861,719, 4,980,289, 5,122,767, and 5,124,263, and PCT patent publications numbers WO 85/05629, WO 89/07150, WO 90/02797, WO 90/02806, WO 90/13641, WO 92/05266, WO 92/07943, WO 92/14829, and WO 93/14188.

Generation of "producer cells" is accomplished by introducing retroviral vectors into the packaging cells. Examples of such retroviral vectors are found in, for example, Korman, et al., Proc. Natl. Acad. Sci. USA. 84:2150-2154, 1987; Morgenstern, et al., Nucleic Acids Res. 18:3587-3596, 1990; U.S. Pat. Nos. 4,405,712, 4,980,289, and 5,112,767; and PCT patent publications numbers WO 85/05629, WO 90/02797, and WO 92/07943.

Herpesvirus packaging vectors are commercially available from Invitrogen Corporation, (Carlsbad, Calif.). Exemplary herpesviruses are an α-herpesvirus, such as Varicella-Zoster virus or pseudorabies virus; a herpes simplex virus such as HSV-1 or HSV-2; or a herpesvirus such as Epstein-Barr virus. A method for preparing empty herpesvirus particles that can be packaged with a desired nucleotide segment, for example a nucleotide seupece include SEQ ID NO: 1 or SEQ ID NO: 2, in the absence of a helper virus that is capable to most herpesviruses is shown in Fraefel et al. (U.S. Pat. No. 5,998,208, issued Dec. 7, 1999).

The herpesvirus DNA vector can be constructed using techniques familiar to the skilled artisan. For example, DNA segments encoding the entire genome of a herpesvirus is divided among a number of vectors capable of carrying large DNA segments, e.g., cosmids (Evans, et al., Gene 79, 9-20, 1989), yeast artificial chromosomes (YACS) (Sambrook, J. et al., MOLECULAR CLONING: A LABORATORY MANUAL, 2nd Edition, Cold Spring Harbor Press, Cold Spring Harbor, N.Y., 1989) or E. coli F element plasmids (O'Conner, et al., Science 244:1307-1313, 1989).

For example, sets of cosmids have been isolated which contain overlapping clones that represent the entire genomes of a variety of herpesviruses including Epstein-Barr virus, Varicella-Zoster virus, pseudorabies virus and HSV-1. See M. van Zijl et al., J. Virol. 62, 2191, 1988; Cohen, et al., Proc. Nat'l Acad. Sci. U.S.A. 90, 7376, 1993; Tomkinson, et al., J. Virol. 67, 7298, 1993; and Cunningham et al., Virology 197, 116, 1993.

AAV is a dependent parvovirus in that it depends on co-infection with another virus (either adenovirus or a member of the herpes virus family) to undergo a productive infection in cultured cells (Muzyczka, Curr Top Microbiol Immunol, 158:97 129, 1992). For example, recombinant AAV (rAAV) virus is made by co-transfecting a plasmid containing the gene of interest, for example, the CD59 gene, flanked by the two AAV terminal repeats (McLaughlin et al., J. Virol., 62(6): 1963 1973, 1988; Samulski et al., J. Virol, 63:3822 3828, 1989) and an expression plasmid containing the wild-type AAV coding sequences without the terminal repeats. Cells are also contacted or transfected with adenovirus or plasmids carrying the adenovirus genes required for AAV helper function. Recombinant AAV virus stocks made in such fashion include with adenovirus which must be physically separated from the recombinant AAV particles (for example, by cesium chloride density centrifugation).

Adeno-associated virus (AAV) packaging vectors are commercially available from GeneDetect (Auckland, New Zealand). AAV has been shown to have a high frequency of integration and infects nondividing cells, thus making it useful for delivery of genes into mammalian cells in tissue culture (Muzyczka, Curr Top Microbiol Immunol, 158:97 129, 1992). AAV has a broad host range for infectivity (Tratschin et al., Mol. Cell. Biol., 4:2072 2081, 1984; Laughlin et al., J. Virol., 60(2):515 524, 1986; Lebkowski et al., Mol. Cell. Biol., 8(10):3988 3996, 1988; McLaughlin et al., J. Virol., 62(6):1963 1973, 1988).

Methods of constructing AAV vectors and using AAV vectors are described, for example in U.S. Pat. Nos. 5,139,941 and 4,797,368. Use of AAV in gene delivery is further described in LaFace et al., Virology, 162(2):483 486, 1988; Zhou et al., Exp. Hematol, 21:928 933, 1993; Flotte et al., Am. J. Respir. Cell Mol. Biol., 7(3):349 356, 1992; and Walsh et al., J. Clin. Invest, 94:1440 1448, 1994.

Recombinant AAV vectors have been used successfully for in vitro and in vivo transduction of marker genes (Kaplitt et al., Nat Genet., 8(2):148 54, 1994; Lebkowski et al., Mol. Cell. Biol., 8(10):3988 3996, 1988; Samulski et al., EMBO J., 10:3941 3950,1991; Shelling and Smith, Gene Therapy, 1: 165 169, 1994; Yoder et al., Blood, 82 (Supp.): 1:347A, 1994; Zhou et al., Exp. Hematol, 21:928 933, 1993; Tratschin et al., Mol. Cell. Biol., 5:3258 3260, 1985; McLaughlin et al., J. Virol., 62(6):1963 1973, 1988) and transduction of genes involved in human diseases (Flotte et al., Am. J. Respir. Cell Mol. Biol., 7(3):349 356, 1992; Ohi et al., Gene, 89(2):279 282, 1990; Walsh et al., J. Clin. Invest; 94:1440 1448, 1994; and Wei et al., Gene Therapy, 1:261 268, 1994).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Identifying Nucleic Acid Ligands Using Gel Electrophoresis

Preparation of Candidate Mixture

DNA oligomers were obtained from a well established library of PCR amplifiable DNA randomers described in Vivekananda et al. (Lab Invest. 86(6):610-618, 2006). This library was custom manufactured at Sigma-Genosys (The Woodlands, Tex.).

Nucleic Acid Ligand Capture

A solution containing infectious prion protein that resulted in chronic waste disease ($PrP^{CWD}$) was loaded into each well of a gradient gel. Native PAGE electrophoresis was performed to immobilize the infectious prion at a position in the gel. After immobilization of the infectious prion at a position in the gel, the concentrated solution of DNA randomers was loaded into each well of the gel. Electrophoresis was performed for a second time so that the DNA randomers would migrate through the gel already having the infectious prions immobilized at a position in the gel. Per each well, 25 μL of the prion protein solution and 25 μL of DNA oligomer solution containing 3.9 μg DNA were sequentially applied and electrophoretically resolved.

During the second electrophoretic step, the PrP$^{CWD}$ proteins barely moved in the electrophoretic field and stayed trapped in the network of the gradient gel, while the small DNA oligomers (MW of 21 kDa) were able to migrate towards the positive electrode. Only those DNA oligomers that showed high affinity to PrP$^{CWD}$ and could withstand the effect of dilution by the running buffer and the effect of the electrostatic field remained attached to the target protein. Remaining DNA randomers migrated past the $PrP^{CWD}$ to an end of the gel.

After the second electrophoretic step, the gels were stained with Ethidium Bromide (EB) to detect and quantify DNA oligomer bound to the $PrP^{CWD}$ protein within the gel. After performing the above procedure retention of some small quantities of DNA oligonucleotides located on the $PrP^{CWD}$ entrapped in the gel was observed (FIG. 1). Panel A of FIG. 1 is a control showing an electrophoresis run of only DNA randomers, no protein. Panel B shows gels obtained by sequential application and electrophoresis of protein and DNA randomer solutions. The area of DNA randomer/$PrP^{CWD}$ complexes stained with EB due to presence of DNA is circled.

As shown in FIG. 1 panel B, sub ng quantities of DNA were observed in the area of localization of DNA randomers complexed with $PrP^{CWD}$ protein. This allowed collection and amplification/sequencing of this DNA fraction as a potential candidate for $PrP^{CWD}$ detection. The estimate of the affinity of the retained aptamer was provided using the estimated amounts of $PrP^{CWD}$ (~400 ng, FIG. 1) and nucleic acid ligand (~0.18 ng, FIG. 2), and average molecular weight of the $PrP^{CWD}$ protein of $275\times10^3$ g/mol. Thus, the dissociation constant was determined by Equation 1.

$$K_d=[PrP^{CWD}]\times[\mathrm{Apt}]/[PrP^{CWD}\mathrm{Apt}]/MWPr^{CWD}\mathrm{protein}, \quad \text{Equation 1}$$

where: $[PrP^{CWD}]$ is the equilibrium quantity of the prion protein (ng); [Apt] is the equilibrium quantity of the retained aptamer (ng); $[PrP^{CWD}Apt]$ is the is the equilibrium quantity of the complex of the prion protein and retained aptamer (ng); and $MWPrP^{CWD}$ protein is the molecular weight of the detected $MWPrP^{CWD}$ protien ng/nmol.

$$K_d=400\times0.18/418/(275\times10^3);$$

$$K_d=6\times10^{-5}\ \mathrm{nmol}$$

Nucleic Acid Ligand Isolation

In order to obtain protein free aptamers via PAGE, the zones containing nucleic acid ligands bound to $PrP^{CWD}$ were carefully cut from the polyacrylamide gels and treated with chaotropic agent (2.0 M solution of sodium thiocyanate, NaSCN). A total of three 1×8 cm gel fragments were immersed in 10 mL of the NaSCN solution in a 50 mL Falcon tube and vortexed for 1 hr at ~1000 rpm. The resultant gel-water suspension was filtered through a 0.8 micron cellulose acetate syringe filter. The filtrate was analyzed for the presence of DNA aptamers by PAGE (4-20% gradient gel) with silver staining according to the protocol provided by BioRad Laboratories. DNA 70-randomer was used to serve as standards for this run. As seen in FIG. 2, the DNA nucleic acid ligands were diluted given the faint bands appearing in the gel.

Nucleic Acid Ligand Amplification

The nucleic acid ligands were amplified by PCR in a G-storm thermal cycler at IST. More specifically, PCR amplification was performed by adding the collected nucleic acid ligands, primers, and nuclease free water to the EconoTaq 2× Master Mix (Table 1) and following amplification steps depicted in Table 2.

TABLE 1

PCR reagent composition

| Reagent | Amount (μl) | Concentration | Final Concentration |
|---|---|---|---|
| Lucigen Econotaq 2X Master Mix | 25 | 2X | 1X |
| Primer AP7: TAC GAC TCA CTA TAG GGA TCC (SEQ ID NO: 3) | 1.0 | 50 pmol/μl | 1 pmol/μl |
| Primer AP3: AAC CCT CAC TAA AGG GAA TT (SEQ ID NO: 4) | 1.0 | 50 pmol/μl | 1 pmol/μl |
| Nucleic acid ligand: 5'-TAC GAC TCA CTA TAG GGA TCC-(N = 28)-GAA TTC CCT TTA GTG AGG GTT-3' (SEQ ID NO: 5) | 1.0 | ~1 ng/μl | <1 ng/μl |
| Nuclease Free Water | 22.0 | — | — |

TABLE 2

PCR steps

| Cycling step | Temperature (° C.) | Time | # of Cycles |
|---|---|---|---|
| Initial Denaturation | 95 | 2 min | 1 |
| Denaturation | 95 | 30 sec | 30 |
| Annealing* | 50-65 *52.9 | 30 sec | 30 |
| Extension | 72 | 30 sec | 30 |
| Final Extension | 72 | 5 min | 1 |
| Hold | 4 | overnight | 1 |

*Optimum annealing temperature

In this manner 4.0 mL solution containing 100 μg of >80% pure nucleic acid ligands was generated (FIG. 3, Lane B).

Nucleic Acid Ligand Identification

The PCR amplification provided amplified material that was sequenced at Sequegen Inc, Worcester, Mass. The obtained nucleic acid ligand sequences were used to generate micromole quantities of the purified nucleic acid ligand sequences at Sigma-Genosys (The Woodlands, Tex.). The sequences of the obtained nucleic acid ligands were as follows:

(SEQ ID NO: 1)
TACGACTCACTATAGGGATCCGTTTTTCCGTACTTCTTAAATCGAATTC

CCTTTAGTGAGGGTT;

(SEQ ID NO: 2)
TACGACTCACTATAGGGATCCTTCTCCGCACTACTTTACCTCGAGTGCT

ATTCCCTTTAGTGAGGGTT.

Nucleic Acid Ligand Affinity and Specificity Assay

To evaluate the specificity of the generated DNA nucleic acid ligands, quantitative real-time PCR (qrt-PCR) was used to quantify low amounts of bound nucleic acid ligand from PrP$^{CWD}$ positive biological samples. The following process was used:

1. Diluted the elk strain of CWD prions (designated as E2) used in the nucleic acid ligand isolation protocol in PBS from 1:10 to 1:100,000.
2. 1:10 dilutions of uninfected normal brain homogenate (NBH) were used as negative controls.
3. 20 μL of each dilution sample was incubated with 180 μL of 1 μM of two different nucleic acid ligand (SEQ ID NO: 1 and SEQ ID NO: 2) for twenty minutes at room temperature.
4. Unbound nucleic acid ligands were removed from the samples by dilution with 300 μL PBS and filtration through a 100 Kd spin column.
5. Step 4 was repeated twice, substituting 500 μL 500 mM NaSCN for PBS.
6. Samples were concentrated to fifty microliters, and nucleic acid ligands purified using the DNeasy blood and tissue kit (Qiagen).
7. Nucleic acid ligands were eluted from columns with 50 μL Tris-EDTA buffer and ten microliters used for nucleic acid ligand detection by real-time PCR using primers specific for nucleic acid ligands and SYBR Green fluorescent DNA-intercalating dye.
8. Two HOH-only samples were used as negative controls for PCR.
9. All samples were incubated for one pre-melt cycle for three minutes at 95° C., then thirty cycles of twenty seconds at 95° C. and 45 seconds at 50° C. for annealing and extension and a final cycle for five minutes at 50° C.

After forty PCR cycles, both negative HOH controls (cyan and green traces (FIG. 4) and Table 3) remained below fluorescent detection threshold (orange horizontal line). The 1:10 E2 dilutions were off the scale where the fluorescence signal was detected without the need for amplification ($C_T$=0). All other E2 dilutions were detected with $C_T$ values of 11.7 for 1:100 to 20.3 for 1:100 000 dilutions. Background detection of nucleic acid ligands eluting with the NBH dilutions (red and blue traces, FIG. 4) was easily distinguished from all other samples, which were well above 1000 relative fluorescence units. Table 3 summarizes the results shown in FIG. 4.

TABLE 3

Figure 1A:
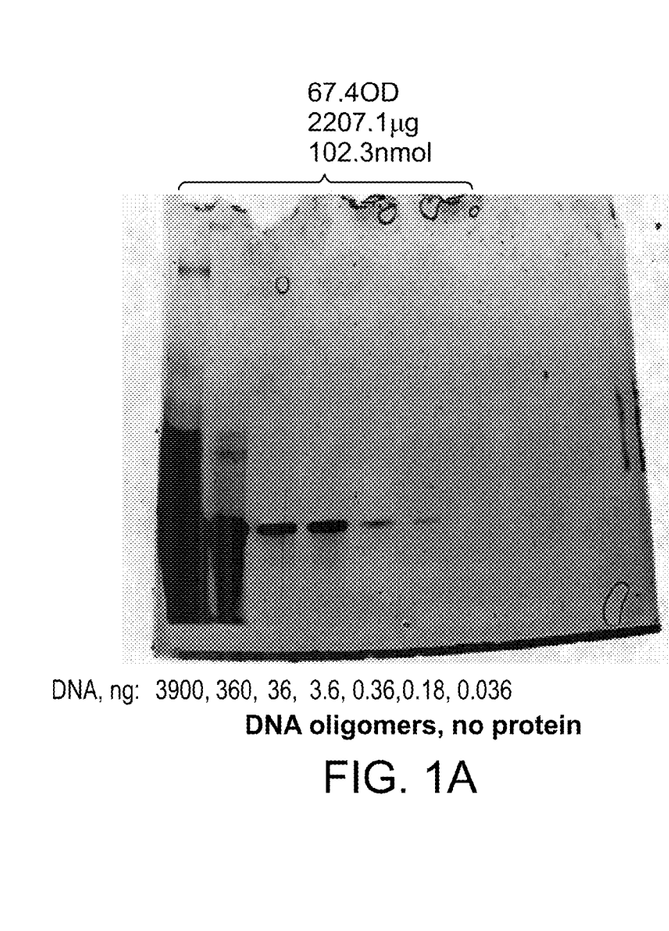
Figure 1B:
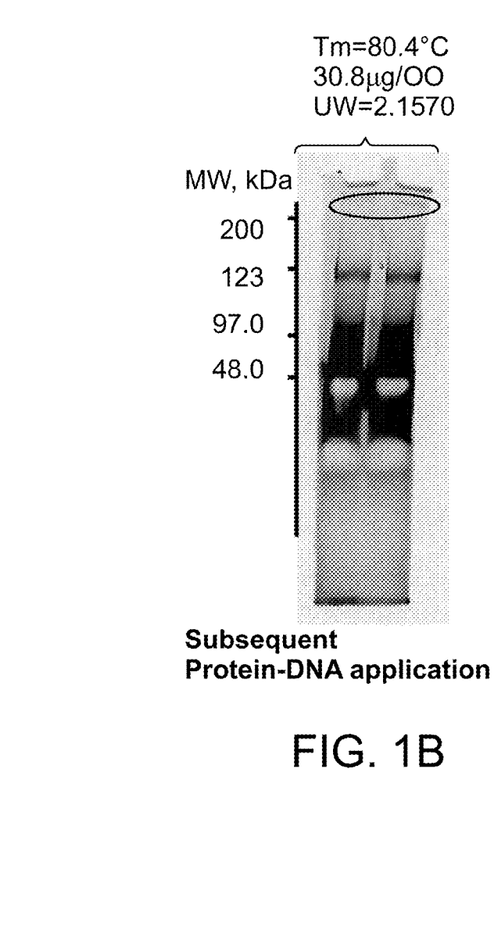
Figure 2:
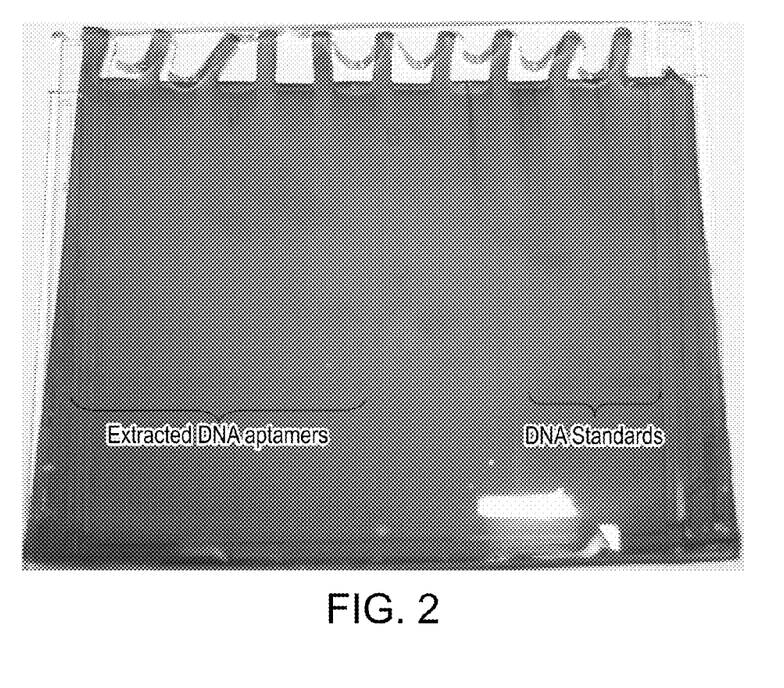
FIG. 2 is a photograph of a gel containing the extracted DNA nucleic acid ligands. Separation was obtained by PAGE electrophoresis.
Figure 3:
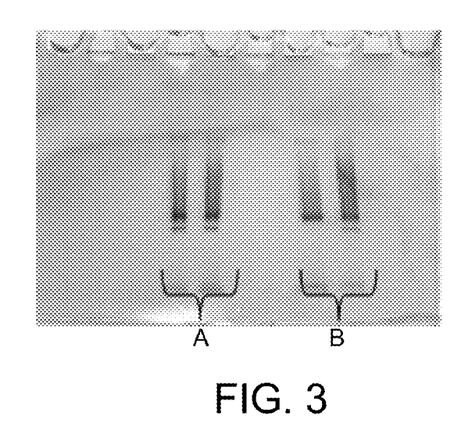
FIG. 3 is a photograph of a gel showing PCR product. Lane A represents amplified starting DNA oligomers and Lane B represents amplified prion specific oligomers.
Figure 4:
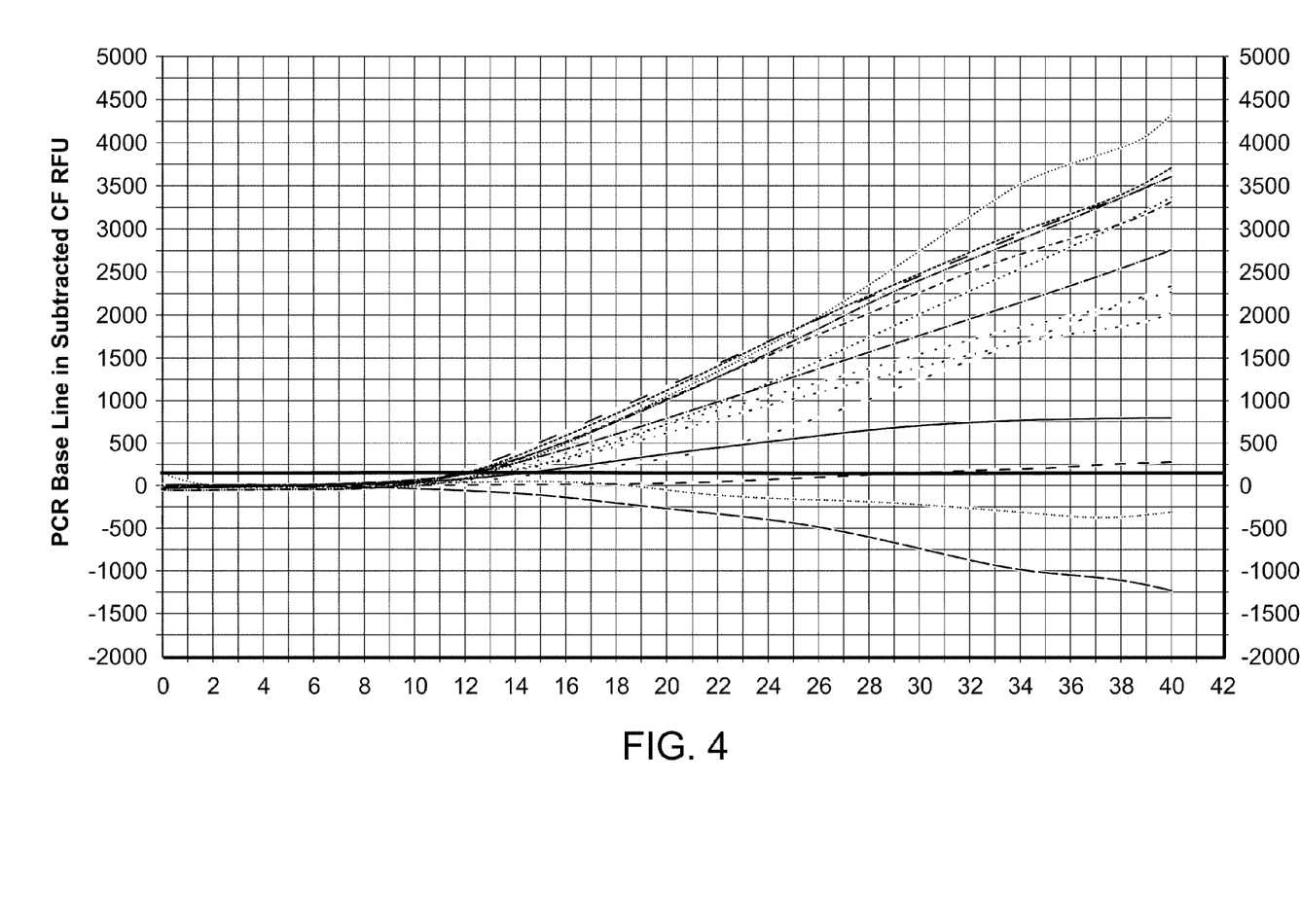
FIG. 4 is a graph showing results of RT-PCR of nucleic acid ligands that were dissociated from $PrP^{CWD}$.

$C_T$ values for RT-PCR samples

| Well | Identifier | Ct |
|---|---|---|
| A01 | HOH | N/A |
| A02 | HOH | N/A |
| B01 | 1:10 E2 (SEQ ID NO: 1) | 0 |
| B02 | 1:10 E2 (SEQ ID NO: 2) | 0 |
| C01 | 1:100 E2 (SEQ ID NO: 1) | 11.7 |
| C02 | 1:100 E2 (SEQ ID NO: 2) | 11.4 |
| D01 | 1:1000 E2 (SEQ ID NO: 1) | 11.4 |
| D02 | 1:1000 E2 (SEQ ID NO: 2) | 12.3 |
| E01 | 1:10,000 E2 (SEQ ID NO: 1) | 13.3 |
| E02 | 1:10,000 E2 (SEQ ID NO: 2) | 15.7 |
| F01 | 1:100,000 E2 (SEQ ID NO: 1) | 20.3 |
| F02 | 1:100,000 E2 (SEQ ID NO: 2) | 16.4 |
| G01 | 1:10 NBH (SEQ ID NO: 1) | 17.4 |
| G02 | 1:10 NBH (SEQ ID NO: 2) | 28.4 |

In Table 3, the $C_T$ values represented the number of cycles required for the fluorescence signal to cross the set threshold. A $C_T$ value ≤29 indicated an abundance of the target, a $C_T$ value of 30-37 indicated a positive detection of the target, and a $C_T$ value of 38-40 indicated the presence of a weak or small amount of the target.

This data show that the two nucleic acid ligands identified by methods of the invention successfully detected up to a 100,000-fold dilution of E2 CWD prions. This detection threshold is at least 100-fold greater than detection by conventional western blotting. Further advances in optimization of the assay to achieve a detection limit to 1,000,000 dilutions of the prion sample are described below.

To simulate the real low pg and fg concentrations of infectious prions in bodily fluids, the affinity of the DNA nucleic acid ligands was further evaluated at 1:100,000 dilutions of brain homogenate (actual working dilution of 1.25×10$^6$ under the established PCR protocol). This dilution level represents a target sample concentration 0.3 pg/mL of PrP$^{Sc}$ in the tested brain homogenate which is well within the range of infectious prion levels found in the blood of live animals (Brown et al., J Lab Clin Med, 137(1):5-13, 2001). Therefore, this sensitivity provides for tests to be conducted on bio-fluids collected from live animals. For example, the concentration of the infectious prions in the blood of infected animals can be estimated at sub pg/mL levels, while the threshold of sensitivity for the detection of infectious prions extracted from scrapie-infected hamster brain has been estimated at 5 pg/mL (Brown et al., J Lab Clin Med, 137(1):5-13, 2001). The estimated concentration of PrP$^{Sc}$ in the urine of infected test animals has been estimated in the fg/mL (0.001 pg) levels (Gonzalez-Romero et al., FEBS Lett, 582(21-22):3161-3166, 2008). Therefore, the DNA nucleic acid ligands developed above can be used to detect infectious prions in about 10 μL of blood or 1 mL of urine.

Data obtained at the 1,000,000 dilutions showed that the infectious prions were detected (total 1.25×10$^6$ dilution) of the tested specimen. This corresponds to significant improvement of the detection limit to 0.025 pg/mL or 250 atto-grams in a 10 μL sample.

The detection of infectious prions in the 1:100,000 dilutions ($C_T$ of 16.4-20.3) are comparable to the low-level detection of nucleic acid ligands in the NBH samples (blue and red traces, $C_T$ of 17.4-28.4) which were at 1:10 dilutions. In addition, the relative fluorescent signals of the NBH samples were much lower and easily distinguishable from test samples (see FIG. 4). These data also showed that optimization removes the low-level detection of the NBH sample altogether. The fluorescence signal of the NBH samples at 1:100 dilutions would be extremely weak to non-existent.

Figure 5:
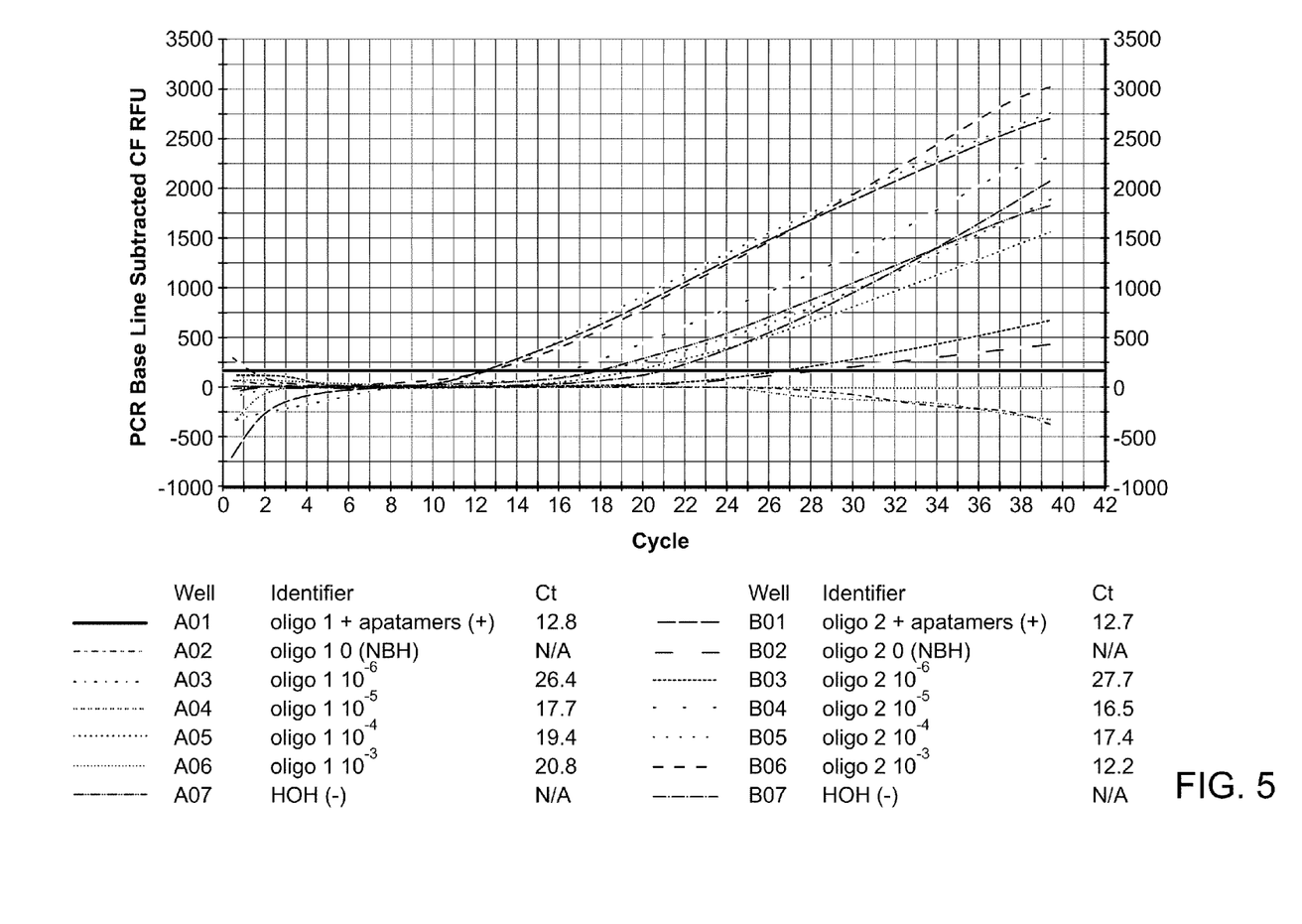
FIG. 5 is a graph showing nucleic acid ligand detection of $PrP^{CWD}$ using DNAse I treatment to remove unbound nucleic acid ligands.

To completely eliminate background nucleic acid ligand noise in the samples, the samples were further treated with ten units of DNAse I for one minute to remove unbound nucleic acid ligands, while PrP$^{CWD}$-bound nucleic acid ligands were protected from digestion. Samples were then treated with 50 μg/mL proteinase K (PK) to eliminate DNAse I activity, then heat inactivated PK for ten minutes at 95° C. to maintain integrity and activity of the Taq polymerase used in the RT-PCR amplification of bound nucleic acid ligands. This DNAse I/PK/heat inactivation protocol completely eliminated possible background amplification of nucleic acid ligands in our negative control samples (FIG. 5) and obviated the need not only for NaSCN treatment and filtration, but also for nucleic acid ligand purification using the DNEasy tissue kit. The DNAse I and PK treatment greatly decreased the organic complexity of the samples, which could be used directly in the QRT-PCR reaction without the time and expense of further DNA extraction. The entire assay was completed from nucleic acid ligand incubation to RT-PCR to data analysis, in less than three hours. CWD prions were successfully detected in a 10$^{-6}$ dilution of brain homogenate from a CWD-infected elk, corresponding to a thousand-fold increase in sensitivity over conventional proteinase K digestion/western blotting. Data also show prion detection in archived spleen tissue from mice infected with CWD (Table 4).

TABLE 4

Summary of additional data generated from subsequent binding assays

| Sample | Prion[1] | Dilution[2] | Detection[3] |
|---|---|---|---|
| Brain | Spiked | $10^{-2}$ | + |
| Brain | Spiked | $10^{-3}$ | + |
| Brain | Spiked | $10^{-4}$ | + |
| Brain | Spiked | $10^{-5}$ | + |
| Brain | Spiked | $10^{-6}$ | + |
| Brain | Infected | $10^{-3}$ | + |
| Brain | Negative | $10^{-1}$ | − |
| Brain | Negative | $10^{-2}$ | − |
| Brain | Negative | $10^{-3}$ | − |
| Spleen | Infected | $10^{-1}$ | + |
| Spleen | Negative | $10^{-1}$ | − |

Figure 6A:
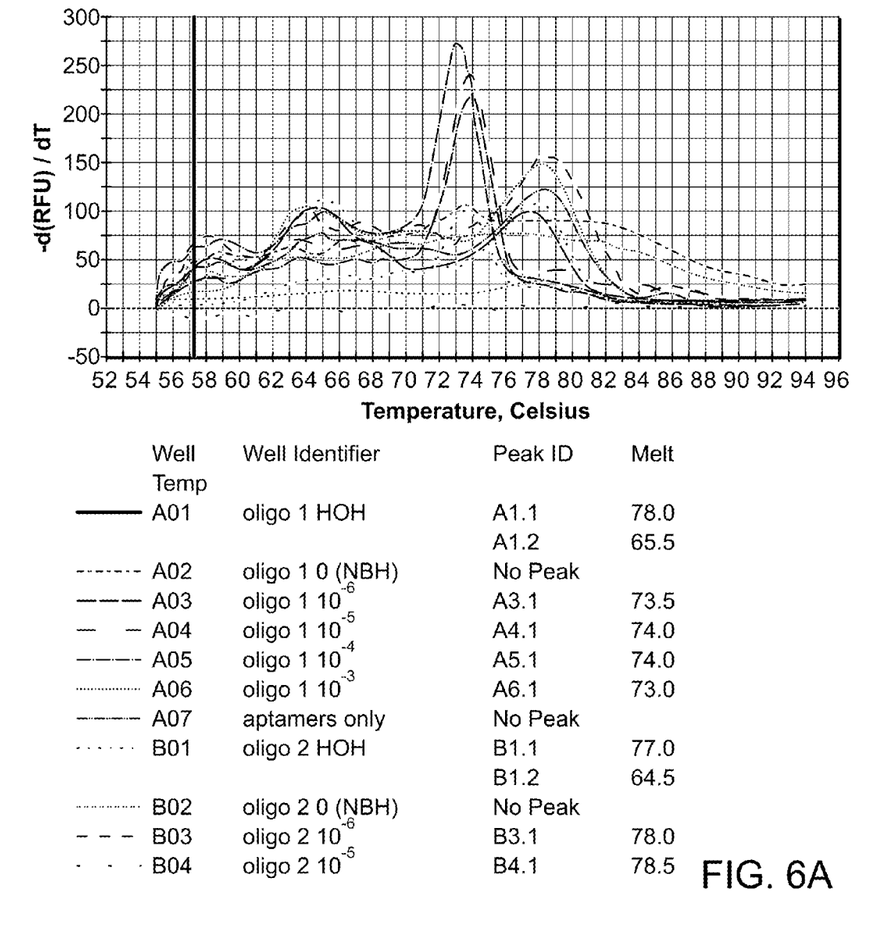
Figure 6B:
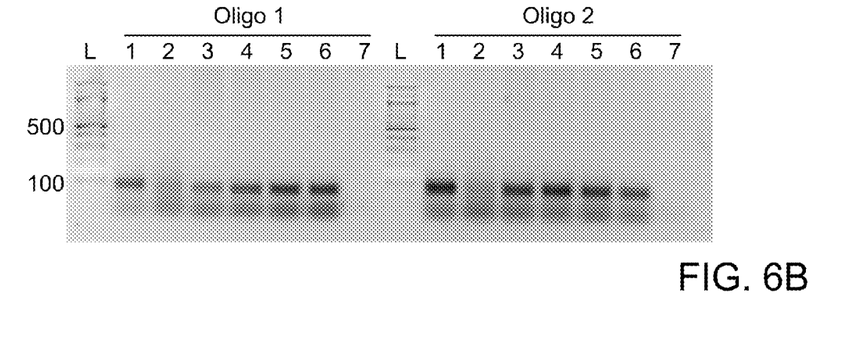

Generation of the specific nucleic acid ligand PCR products were confirmed by both melt curve analysis (FIG. 6 panel A) and agarose gel electrophoresis (FIG. 6 panel B) of amplified samples.

Data herein show that the selected DNA nucleic acid ligands generated by methods of the invention could detect infectious prions at levels as low as 0.03 pg/mL concentrations directly in 20 µL samples of biological specimens. This sensitivity is at least 1000-fold higher than what is achievable in immuno-enzymatic assays. Data herein further show the specificity of these DNA nucleic acid ligands for infectious prions over normal prions. There were no false positive or negative reactions in controls containing normal prion protein or no prion protein.

These results show that DNA nucleic acid ligands generated by methods of the invention can detect very low concentrations of infectious prion that are representative of concentrations found in biological fluids or samples such as blood, urine and feces.

What is claimed is:

1. An isolated nucleic acid ligand that binds to an infectious prion, wherein the nucleic acid ligand comprises the nucleotide sequence of SEQ ID NO: 1 or the nucleotide sequence of SEQ ID NO: 2.

2. The nucleic acid ligand according to claim 1, wherein the nucleic acid ligand is single stranded.

3. The nucleic acid ligand according to claim 1, wherein the nucleic acid ligand is DNA.

4. The nucleic acid ligand according to claim 1, wherein the nucleic acid ligand is RNA.

5. The nucleic acid ligand according to claim 1, further comprising a detectable label.

6. The nucleic acid ligand according to claim 5, wherein the detectable label is a fluorescent label.

* * * * *

SEQUENCE LISTING

```
<160> NUMBER OF SEQ ID NOS: 5

<210> SEQ ID NO 1
<211> LENGTH: 64
<212> TYPE: DNA
<213> ORGANISM: Artificial Sequence
<220> FEATURE:
<223> OTHER INFORMATION: Nucleic acid ligand against infectious prions

<400> SEQUENCE: 1
tacgactcac tatagggatc cgtttttccg tacttcttaa atcgaattcc ctttagtgag      60
ggtt                                                                   64

<210> SEQ ID NO 2
<211> LENGTH: 68
<212> TYPE: DNA
<213> ORGANISM: Artificial Sequence
<220> FEATURE:
<223> OTHER INFORMATION: Nucleic acid ligand against infectious prions

<400> SEQUENCE: 2
tacgactcac tatagggatc cttctccgca ctactttacc tcgagtgcta ttcccttag       60 tgagggtt                                                               68

<210> SEQ ID NO 3
<211> LENGTH: 21
<212> TYPE: DNA
<213> ORGANISM: Artificial Sequence
<220> FEATURE:
<223> OTHER INFORMATION: Primer AP7

<400> SEQUENCE: 3
tacgactcac tatagggatc c                                                21

<210> SEQ ID NO 4
<211> LENGTH: 20
<212> TYPE: DNA
<213> ORGANISM: Artificial Sequence
<220> FEATURE:
<223> OTHER INFORMATION: Primer AP3

<400> SEQUENCE: 4
aaccctcact aaagggaatt                                                  20
```

```
<210> SEQ ID NO 5
<211> LENGTH: 70
<212> TYPE: DNA
<213> ORGANISM: Artificial Sequence
<220> FEATURE:
<223> OTHER INFORMATION: Nucleic acid ligand
<220> FEATURE:
<221> NAME/KEY: misc_feature
<222> LOCATION: (22)..(49)
<223> OTHER INFORMATION: n is a, c, g, or t

<400> SEQUENCE: 5
tacgactcac tatagggatc cnnnnnnnnn nnnnnnnnnn nnnnnnnnng aattcccttt    60
agtgagggtt                                                          70
```